United States Patent
Frangi

(10) Patent No.: US 7,955,287 B2
(45) Date of Patent: Jun. 7, 2011

(54) ORTHOPAEDIC SUPPORT FOR IMMOBILIZING THE THUMB

(76) Inventor: Gianluigi Frangi, Bodio Lomnago (IT)

( * ) Notice: Subject to any disclaimer, the term of this patent is extended or adjusted under 35 U.S.C. 154(b) by 661 days.

(21) Appl. No.: 11/913,355

(22) PCT Filed: May 3, 2005

(86) PCT No.: PCT/IT2005/000253
§ 371 (c)(1),
(2), (4) Date: May 9, 2008

(87) PCT Pub. No.: WO2006/117808
PCT Pub. Date: Nov. 9, 2006

(65) Prior Publication Data
US 2009/0012438 A1 Jan. 8, 2009

(51) Int. Cl.
*A61F 5/00* (2006.01)
*A61F 13/00* (2006.01)
(52) U.S. Cl. ............ 602/22; 602/5; 602/6; 602/60; 602/61
(58) Field of Classification Search ............ 602/5, 20, 602/21, 22; 2/21, 181.1, 161.2, 161.3, 161.6, 2/22; D24/190–192
See application file for complete search history.

(56) References Cited

U.S. PATENT DOCUMENTS

| 2,388,330 | A | * | 11/1945 | Jungmann ............... 2/16 |
| 2,477,126 | A | * | 7/1949 | Hartmann ............ 128/880 |
| 2,523,606 | A | * | 9/1950 | Young ................... 602/7 |
| 4,524,464 | A | * | 6/1985 | Primiano et al. .......... 2/16 |
| 4,768,502 | A | * | 9/1988 | Lee ..................... 602/6 |
| 4,840,168 | A |   | 6/1989 | Lonardo et al. |
| 4,862,877 | A |   | 9/1989 | Barber |
| 5,787,896 | A | * | 8/1998 | Sackett ............... 128/880 |
| D405,180 | S | * | 2/1999 | Reina ................ D24/190 |
| 5,899,870 | A |   | 5/1999 | Deirmendjian et al. |
| 6,325,772 | B1 | * | 12/2001 | Scheuermann et al. ...... 602/22 |
| D558,883 | S | * | 1/2008 | Ortiz ................ D24/190 |
| 2003/0191421 | A1 |   | 10/2003 | Weaver et al. |

* cited by examiner

Primary Examiner — Kim M Lewis
(74) Attorney, Agent, or Firm — Connolly Bove Lodge & Hutz LLP

(57) ABSTRACT

A support (1) of a rigid material having a salient arcuate bow (6) extending orthogonally from one side of the vertex of a saddle portion (5) has a Velcro® hook part (2) fixed onto the concave surface of the saddle portion (5) and a coating of a cushioning material (3) on the convex surface of the salient arcuate bow (6). The support (1) is fixable onto a wrist band (P) by anchoring the Velcro® hook part (2) present on the concave surface of the saddle (5) onto a textile lace (9) of the wrist band (P) passed in front of the thumb, the coated convex surface of the salient arcuate bow (6) sustaining the thumb resting on it. A textile binding lace (7) is wound around the thumb and the sustaining salient arcuate bow (6) of the saddle (5) for immobilizing the thumb.

4 Claims, 2 Drawing Sheets

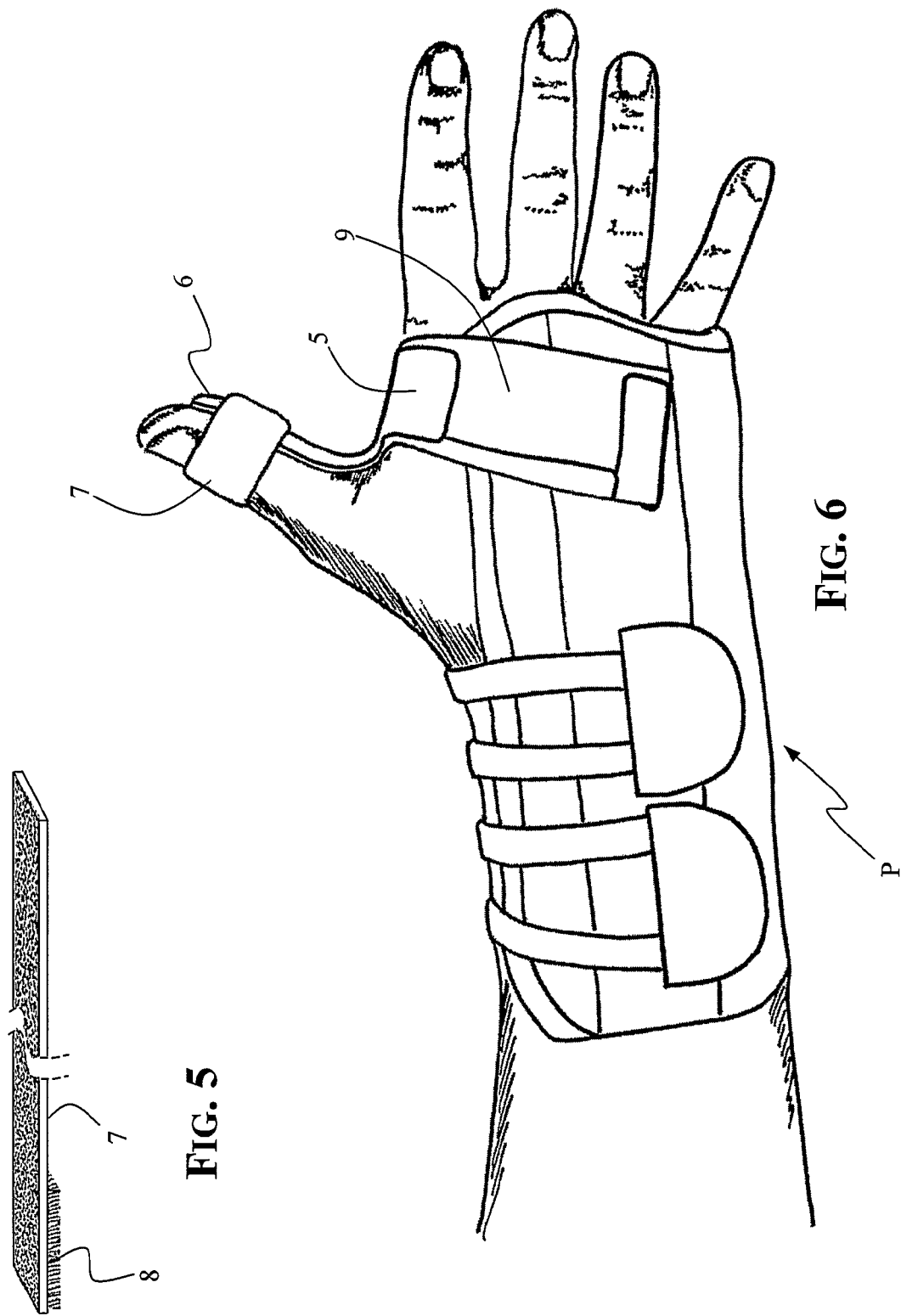

ORTHOPAEDIC SUPPORT FOR IMMOBILIZING THE THUMB

RELATED APPLICATIONS

This application is a national stage application (under 35 U.S.C. §371) of PCT/IT2005/000253 filed May 3, 2005, disclosure of which is incorporated herein by reference.

BACKGROUND OF DISCLOSURE

1. Technical Field

The present invention relates in general to orthopaedic protections and supports and in particular to orthopaedic implements for immobilizing the thumb of a hand.

2. Description of Related Art

Commonly, when the thumb of a hand must be immobilized, for example during therapies for curing injuries or fractures or during post-surgery recovery, it is a common medical practice to apply a plaster casting around the wrist and thumb articulations in order to keep the thumb in a suitably distended position. After a first post-traumatic or post-surgery period that may necessarily require a rigid casting, the therapy may contemplate alternative forms of thumb immobilization to be maintained for a further recovery period and eventually also during the phase of re-habilitation, for re-establishing satisfactory functionality of the interested articulation, in order to prevent risks of accidental stresses that could prejudice the progress of the re-habilitation.

These alternative forms of immobilization of the thumb may, in some cases, substitute the plaster casting itself, for example in case of minor injuries or surgeries.

These alternative orthopaedic supports for immobilizing the thumb of a hand basically includes a modified wrist band to be tightened around the wrist and thumb base generally provided with a special rigid structure generally including a metallic reinforcement core anchored in the wrist band and projecting up to constitute an arcuate projecting arm to which the thumb may be fastened by textile laces commonly provided with Velcro® fastener parts so that the back of the thumb can be securely held against a concave lower surface of the arcuate extension, from which it will remain stably suspended.

These purposely modified wrist bands have the drawback of needingly be produced distinctly for right hands and for left hands, thus requiring a duplication of inventories along the production and commercial distribution line of these articles.

Another drawback is their relative complexity due to the need to form such an arcuate projection rendered substantially rigid by a metal core, in an otherwise common textile structure of a normal wrist band to be worn around the wrist articulation.

The right hand or left hand singularity of the support and its relative structural complexity increase considerably its cost. Moreover, such a special orthopaedic support would remain too awkward to use for the sole wrist articulation.

Moreover, the tightening of the back of the thumb against the lower surface of the rigid arcuate extension tends to cause irritation and pains at points of concentration of the compression on the back of the thumb so tightened against the rigid support.

To these inconveniences and drawbacks of the above discussed known orthopaedic supports for the immobilization of the thumb of a hand, the present applicants have found an extremely simple and effective solution.

BRIEF SUMMARY OF DISCLOSURE

The novel thumb immobilization support of the present applicants uses a common textile wrist band, normally fabricated for being applicable around the wrist articulation of a left hand or of a right hand and commonly having a textile retention lace that extends from an edge of the textile body of the wrist band to be passed in front of the thumb and taughtly anchored, usually by a Velcro® hook part (meaning with this expression the part of a Velcro® fastening device characterized by a multitude of tiny needles bent at the tip that is engageable on a pad surface of a fabric woven with loops of a monofilament thread) present at its free end, over the outer surface of the textile body of the wrist band. The only requisite being that the outer surface of the textile wrist band, at least in the area of anchorage of the free end of the retention lace be structurally suitably or be provided with a pad suitable to anchor the Velcro® hook part.

Basically, the implement of this invention is constituted by a saddle of a substantially rigid material, having a salient arcuate bow extending from one side of the vertex of the saddle, a Velcro® with a hook part fixed on at least the concave surface of the saddle and preferably also on the concave surface of the salient curved arm, and a coating of a soft cushioning material, for example of soft silicon rubber or equivalent elastomer, on the convex surface of the salient arcuate bow.

The saddle is installed onto the retention textile lace passing in front of the thumb of the wrist band, by anchoring thereon the Velcro® hook part present on the concave surface of the saddle such that the convex surface of the salient arcuate bow, coated with comfortably cushioning material sustains the thumb resting on it.

According to the preferred embodiment, a textile binding lace may be anchored at an extremity on the Velcro® hook part present on the concave surface of the salient arcuate bow and has at the other extremity a Velcro® hook part such to be wound around the back of the thumb resting on the soft material coating of the salient arcuate bow, bringing the free end of the lace provided with the Velcro® hook part to overlap its anchored extremity for anchoring its free end thereon, for immobilizing the thumb.

The rigid material with which the saddle and with the salient arcuate bow may be made can be metal, for example an aluminum or a steel sheet patterned by die stamping and successively bent to shape in suitable mold or directly shaped and stamped by using suitable drawing and stamping tool.

The curvature of the salient arm and/or of the saddle itself may be in some measure modified by forcibly deforming the shaped metal.

Alternatively, the saddle with a salient arcuate bow may be made of a thermoplastic material, for example by injection molding. In this case, an eventual modification of curvature may be obtained by heating the article before forcibly adapting its curvature as desired.

The saddle may be applied on a worn wrist band by positioning it and pressing the Velcro® hook part onto the textile lace that is commonly passed in front of the thumb and taughtly fixed onto the wrist band to retain it in place independently on the fact that the wrist band be worn around the wrist articulation of a right or a left hand.

Therefore, the implement of this invention constituted by the saddle and by at least a textile bringing lace of immobilization of a thumb can be used for immobilizing the thumb of a right or of a left hand.

This coupled to the fact that a common wrist band can also be worn either on a right hand wrist or on a left hand wrist, eliminates completely the burden of double inventories.

The relatively sensitive back of the thumb is no longer tightened against a rigid support of immobilization as in the known implements, on the contrary it comfortably rests on a cushioned surface of the salient arcuate bow of the saddle. The rest position of the thumb over the curved arm support may be adapted as needed, by forcibly deforming as required the metal or thermoplastic body of the saddle implement in order to lower or raise the salient arcuate bow giving it the most appropriate curvature. To this end, the shape of the salient arm may have a zone of reduced width at the base of the salient arm for trimming its curvature (inclination).

The invention is defined in the annexed claims.

BRIEF DESCRIPTION OF THE SEVERAL VIES OF THE DRAWINGS

FIG. 5 shows a textile binding lace for immobilizing the thumb once it is rested on the salient arcuate bow of the saddle.

FIG. 6 shows the way in which the implement for immobilizing the thumb of the present invention is applied onto a wrist band.

DETAILED DESCRIPTION OF THE DISCLOSURE

Figure 1:
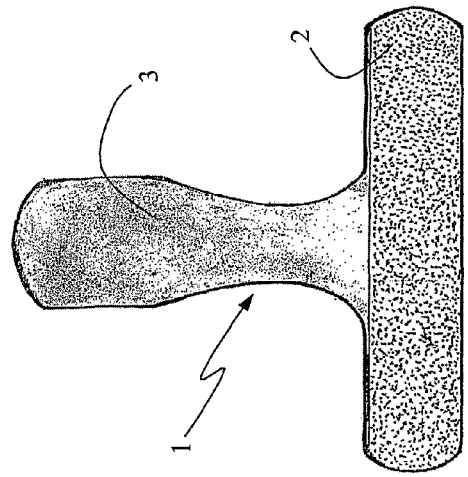
FIG. 1 and FIG. 2 are views of the opposite faces of the implement of the present invention still in flat form while being fabricated.
Figure 2:
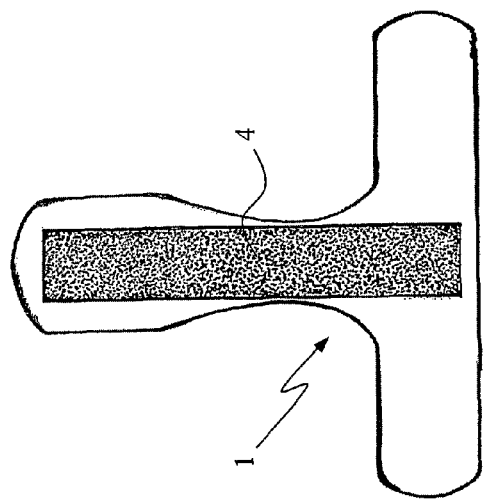

As may be observed in the two views of FIGS. 1 and 2, relative to an embodiment employing a metal plate of appropriate rigidity/ductility, for example of aluminum sheet, that is die stamped for obtaining a substantially "T" shaped piece.

A strip 2 of a hook part of a Velcro® fastening device is permanently bonded on the horizontal upper bar of the "T" shape of a face of the "T" shaped stamped plate, by an appropriate adhesive or fixed thereon with any other suitable means, for example by a plurality of small rivets. On the contrary, over the stem portion of the "T" shape is applied a coating of a cushioning material, for example of a soft silicon rubber 3.

According to a preferred embodiment, also on the other face of the "T" shaped article of manufacture, visible in FIG. 2, may be applied a strip 4 of a hook part of a Velcro® fastening device, extending for almost the whole length of the stem portion of the "T" shape.

Also in this case, the Velcro® hook part 4 may be permanently bonded by a suitable adhesive or fastened with any other suitable means, for example by a plurality of small rivets.

Figure 3:
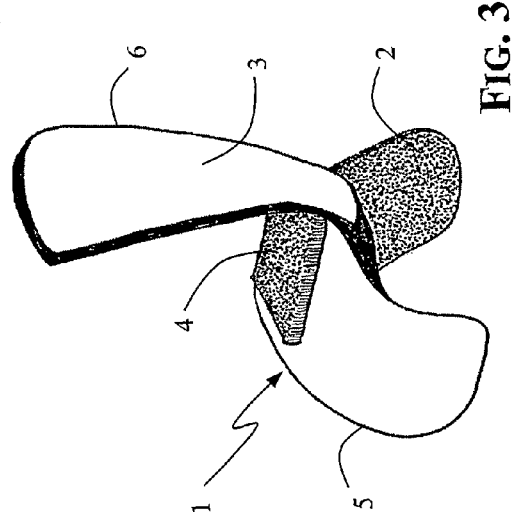
FIGS. 3 and 4 are a three-dimensional and a front view, respectively, of the saddle with salient arcuate bow after having been completely shaped.
Figure 4:
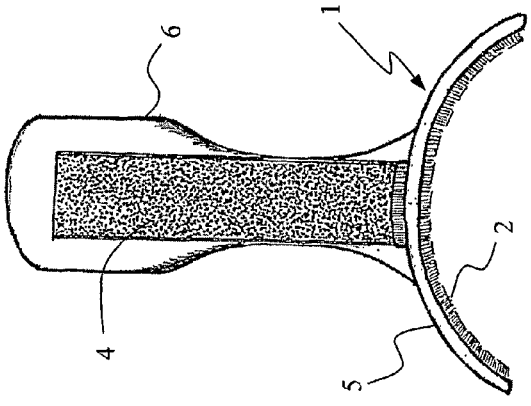

As shown in FIGS. 3 and 4, to the flat article of manufacture of FIGS. 1 and 2 a definitive shape is given by curving the horizontal bar portion of the "T" shape to form a saddle 5 and by curving the stem portion of the "T" shape to form a salient arcuate bow 6 extending from one side of the vertex of the saddle 5.

Alternatively, the silicon rubber coating 3 as well as the two strips 2 and 4 of Velcro® hook part may be applied to the respective surfaces of the support 1, after receiving its definitive shape.

As a matter of fact, it is even possible to form the support 1 already shaped as illustrated in FIGS. 3 and 4, though a single operation, by a drawing-stamping process using appropriate dies for forming and stamping the support 1 in its final shape.

FIG. 5 shows a textile binding lace 7 provided with a Velcro® hook part 8 at one end and with a surface suitable to receive and engage the tiny hooks of the Velcro® part 8.

FIG. 6 shows a common textile wrist band P worn around the wrist articulation of a hand and having a retention lace 9 passed in front of the thumb and taughtly fixed (typically by a Velcro® hook part carried at one end) onto the outer surface of the textile tubular body of the wrist band, according to a common design of these textile orthopaedic protections.

The saddle 5 of the support 1 of the present invention is stably fixed on the surface of the retention lace 9 of the wrist band by anchoring thereon the Velcro® hook strip 2 present on the concave surface of the saddle 5.

As may be observed, the thumb rests on the surface cushioned by the silicon rubber coating 3 of the salient arcuate bow 6.

Immobilization of the thumb so sustained by the soft material coated arm 6 of the support 1, is ensured by anchoring one end of the textile binding lace 7 onto the Velcro® hook strip 4 present on the concave surface of the arm 6, winding the lace 7 around the back of the thumb resting on the arm 6, until bringing the Velcro® hook part 8 present at the free end of the textile lace 7 to overlap the end previously anchored of the same textile lace and fixing it over the anchored end, thus immobilizing the thumb resting on the salient arcuate bow 6 of the saddle 5.

Of course, it will be possible to use more than one textile binding lace 7, for a most secure immobilization and/or for added protection.

As may be easily observed, the orthopaedic support for immobilizing the thumb is an implement distinct from the common wrist band P on which is applicable and is separable from it when not being used.

This renders the wrist band usable even when there is not the need of immobilizing the thumb either on the right hand or a left hand.

The thumb immobilization orthopaedic support, essentially constituted by the saddle shaped body with the salient arcuate bow and by one or more textile binding laces, is usable by installing it on a common textile wrist band, whenever the thumb of a hand should be immobilized.

The invention claimed is:

1. An orthopedic support for immobilizing the thumb of a hand employing a wrist band worn around the wrist articulation and having at least a textile lace that is passed in front of the thumb and taughtly fixed onto the external surface of the wrist band, characterized by comprising
   a saddle of a rigid material having a concave surface, a vertex and having a salient arcuate bow extending orthogonally from one side of the vertex of the saddle;
   a fabric hook- and loop-fastener having the hook part fixed onto the concave surface of said saddle;
   a coating of a cushioning material on the convex surface of said salient arcuate bow; said saddle being fixable on the wrist band by anchoring said hook part of said fabric hook- and loop-fastener present on the concave surface of the saddle onto said textile lace of the wrist band in front of the thumb, the coated convex surface of said salient arcuate bow sustaining the thumb resting on it;
   at least a textile binding lace adapted to be wound around the thumb and the sustaining salient arcuate bow of the saddle for immobilizing the thumb.

2. The orthopedic support according to claim 1, wherein said rigid material constituting said saddle and said salient arcuate bow is a metal sheet, the curvatures of said saddle and of said salient arcuate bow being modifiable by forcibly deforming the metal sheet.

3. The orthopedic support according to claim 1, wherein said cushioning material is silicon rubber.

4. The orthopedic support according to claim 1, wherein a fabric hook- and loop-fastener hook part is fixed also on the concave surface of said salient arcuate bow and said textile lace has one end anchored on said fabric hook- and loop-fastener hook part present on the concave surface of the salient arm and a fabric hook- and loop-fastener hook part at its free end, for being wound around the back of the thumb until overlapping its anchored end onto which said fabric hook- and loop-fastener hook part is fastened.

* * * * *